United States Patent [19]

Johnson

[11] Patent Number: 4,932,950
[45] Date of Patent: Jun. 12, 1990

[54] SELF-ADJUSTING SUSPENSION SYSTEM FOR PERINEAL SHIELD

[75] Inventor: Russell L. Johnson, Weyauwega, Wis.

[73] Assignee: Weyerhaeuser Company, Tacoma, Wash.

[21] Appl. No.: 203,371

[22] Filed: May 31, 1988

[51] Int. Cl.$^5$ .............................................. A61F 13/16
[52] U.S. Cl. ................................. 604/392; 604/393; 604/400; 604/402
[58] Field of Search ............... 604/392, 393, 396, 397, 604/398, 399, 400, 401, 402

[56] References Cited

U.S. PATENT DOCUMENTS

| | | | |
|---|---|---|---|
| 470,983 | 3/1892 | Carpenter | 604/402 |
| 929,166 | 7/1909 | Plamondon | 604/400 |
| 1,423,353 | 7/1922 | Morner | 604/402 |
| 1,664,626 | 4/1928 | Ito | 604/397 |
| 2,349,392 | 5/1944 | Weber | 604/398 |
| 2,565,738 | 8/1951 | Oellerich | 604/401 |
| 3,156,241 | 11/1964 | Hyde et al. | 604/402 |
| 3,522,808 | 8/1970 | Worcester | 604/401 |
| 3,566,870 | 3/1971 | Berjamin | 604/399 |
| 3,788,323 | 1/1974 | Robinson | 604/402 |
| 4,182,334 | 1/1980 | Johnson | 604/393 |
| 4,315,508 | 2/1982 | Bolick | 604/392 |

FOREIGN PATENT DOCUMENTS

| | | | |
|---|---|---|---|
| 1149104 | 7/1983 | Canada | 604/392 |
| 348366 | 4/1905 | France | 604/397 |
| 474673 | 3/1915 | France | 604/401 |
| 549431 | 2/1923 | France | 604/401 |
| 14917 | of 1906 | United Kingdom | 604/397 |

*Primary Examiner*—C. Fred Rosenbaum
*Assistant Examiner*—Mark O. Polutta

[57] ABSTRACT

The invention is a self-adjusting suspension system which is incorporated into the structure of a perineal shield. A flexible strand is provided at corner locations on the perimeter of the shield. A separate waistband portion has one or more elastic tensioning strips which are slidably connected by followers to the flexible strands at the corners. The follower divides the flexible strand into two directed segments, one to each side of the follower. Each directed segment is oriented towards the adjacent corner location on that side of the follower and secured to the perimeter of the shield. When tension is applied to the followers so that the flexible strands are also placed in tension, the followers slide along the strands until the tensions in the strands to each side of the followers are equal and the tension around the perimeter of the shield is approximately uniform. Substantially no tension is directed towards the midspan of the shield.

7 Claims, 3 Drawing Sheets

SELF-ADJUSTING SUSPENSION SYSTEM FOR PERINEAL SHIELD

FIELD OF THE INVENTION

This invention relates to suspennsion systems for shields to be worn next to the perineal region of the human body. More particularly this invention relates to a low cost, self-adjusting suspension system that provides tensions around the perimeter of a flexible perineal shield while leaving the midspan of the shield untensioned.

A partial list of devices that might employ the suspension system of this invention would include; diapering devices, menstrual protection devices, athletic protection devices, incontinence protection devices, stain protection devices, and modesty preservation devices. These devices may be disposable devices or reuseable devices.

BACKGROUND OF THE INVENTION

Patent records show that for the last century there has been a recognized need for a garment-like system for supporting a shield in the perineal region of the human pelvis.

It has long been known that a successful suspension system for perineal shields would be comfortable to wear, remain reliably in place, be adjustable to a large number of body shapes and positions, and be discreet and inconspicuous in use.

Over the last century there have been numerous attempts to provide both adjustable and self adjusting suspension systems for perineal shields. The failure of these attempts is witnessed by the absence of a commercially successful self adjusting suspension system for perineal shields on the market today.

In recent times, the use of contact adhesive as a fastener has permitted the attachment of sanitary napkins to undergarments and the "fitting" of diapers to a variety of baby anatomies. The advent of these expedients lessened, for a period of time, the need for a self adjusting suspension system. The appearance in the 1970's of disposable shields for use in dealing with urinary incontinence has renewed the search for a better suspension system for perineal shields.

Currently, technologies borrowed from the sanitary napkin, diaper and undergarment arts are used as expedients for supporting perineal shields which serve the needs of those having urinary incontinence problems that are moderate to severe in character.

The use of elastic elements as components of perineal shields and of suspension systems for perineal shields in common in the art. Elastic provides accommodation over a range of dimensions and configurations. This accommodation is often accompanied by changes in pressures and fits and with an attendant change in the comfort and reliability of the unit.

Heretofore, elastic waist bands have been secured to perineal shields at points or along lines at the corners of the shields. Such attachments create tension stresses in the midspan of the shield. Such stresses add to product discomfort and unreliability and are counterproductive in creating and maintaining reservoirs for retaining free liquids until they can be absorbed.

The related patented art of which the inventor is aware is as follows:

| PATENT NO. | INVENTOR | DATE |
|---|---|---|
| 765,074 | Griffith | July 12, 1904 |
| 867,091 | Altermatt | September 24, 1907 |
| 929,166 | Plamondon | July 27, 1909 |
| 979,730 | Argo | December 27, 1910 |
| 1,103,815 | Nesgood | July 14, 1914 |
| 1,159,362 | Cornell | November 9, 1915 |
| 1,182,007 | Glaser | May 9, 1916 |
| 1,329,195 | Martinka | Janurary 27, 1920 |
| 1,616,616 | Friedman | Feburary 8, 1927 |
| 2,211,137 | Lesselbaum | August 13, 1940 |
| 3,993,074 | Murray et al | November 23, 1976 |
| 4,182,334 | Johnson | Janurary 8, 1980 |

All of the above patent references teach the combination of a perineal shield and a suspension system which involve a component that passes between the legs of a wearer and a component that circles all or a part of the lower torso.

All of the reference patents except Friedman and Glaser teach the combination of a suspension system and a shield wherein the shield is separable from the suspension system.

All of the above cited reference patents teach suspension systems that provide a means for applying tensioning forces to a shield and a means for securement of the units around the lower torso of a wearer. The instant invention shares the above described attributes with the prior art.

All of the above references except Martinka, Nesgood, Griffith, and Friedman, teach combination of shields and suspension systems wherein a strand is slidably engaged with a follower element whereby the tensions in the waist element are related to the tensions applied to the shield element. The suspension system of this invention shares these characteristics with the prior art.

A novel feature of the instant invention is that it incorporates into the structure of a perineal shield a means for maintaining a substantially uniform tension around the perimeter of the perineal shield without applying any significant tensions to the midspan of the shield. This feature is of great importance in the containment of rapidly accumulating volumes of urine which are present during an incontinent discharge or urine of moderate to severe character.

SUMMARY OF THE INVENTION

The invention in its simplest form is that of a perineal shield having four corner locations. Each corner location has associated therewith a flexible strand which is slideably engageable with a follower. The follower divides the strand into two segments, a first directed segment that is directed towards a first adjacent corner location, and a second directed segment that is directed towards a second adjacent corner location. When a tensioning force is applied to each of the followers, the followers will move along the strand until the tensions in the strands to each side of the followers are equal and substantially no tensioning forces are transmitted to the midspan of the shield. When the shield is positioned between the legs of a wearer and a suitable tensioning means is attached to the flexible strands at the corner locations, the directed tensions in the strands introduce a uniform force around the perimeter of the shield that creates a continuous, uniform and intimate contact between the perimeter of the shield and the body of the wearer.

It is, therefore, an object of this invention to provide a suspension system for perineal shields that is; comfortable to wear, maintains the shield reliably in place, adapts to a large number of body shapes and configurations, and is discreet and inconspicuous in use.

It is further an object of this invention to provide the suspension system described above wherein the tension system, in use, is self adjusting so as to maintain a substantially uniform tension around the perimeter of a perineal shield at all times while at the same time placing substantially no tension or other stresses on the midspan of the shield lying inside the tensioned perimeter.

It is further an object of this invention to provide the suspension system described above wherein the system is low in cost and convenient to use.

Other objects will be made apparent by the following specifications, drawings and claims.

DETAILED DESCRIPTION OF THE PREFERRED EMBODIMENTS

In the figures, like numbers refer to like objects.

Figure 1:
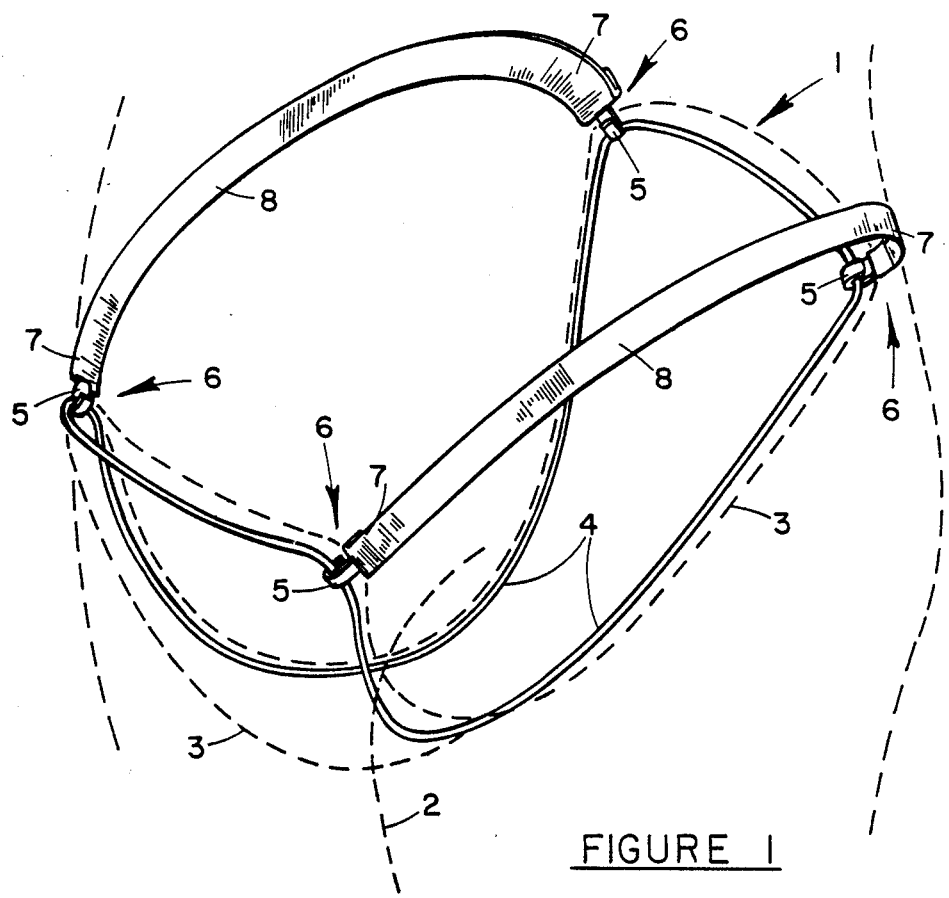
FIG. 1 is a partially schematic pictorial view of the self adjusting suspension system of this invention in one of its simplest forms.

In FIG. 1, self adjusting suspension system 1 is shown in simplified form. The outline of the wearer's anatomy 2 is shown in long dashed lines. The outline of a perineal shield 3 is shown by shorter dashed lines.

It is contemplated that most perineal shields to be used in cooperation with the self adjusting suspension systems of this invention will be generally planar and generally rectangular. However, the suspension systems of this invention need not be limited to planar and/or rectangular shields. For example; the corners of a shield may be rounded, and/or the plan view of the shield may have a generally hourglass shape and the shield may be thicker in the center than it is around the perimeter and the shield may still be functionally served by the self adjusting suspension system of this invention. Therefore, the term "corner location" will herein refer to a portion of the shield that is in the vicinity of a shield that would ordinarily be described as a corner for communicative purposes; i.e., a location near the extremes of length and width. In a like manner "the perimeter of the shield" shall herein refer to the outside edges of the shield and a portion of the shield lying a short distance inward from the outside edges of the shield and the "midspan" of the shield shall refer to the portion of the shield lying inside the perimeter of the shield.

The self-adjusting suspension system 1 of FIG. 1 has a flexible strand 4 which is engaged by a coupling device or follower 5 at corner location 6. Followers 5 are secured to the free ends 7 of tensioning means 8 which are here shown as a pair of elastic strips or bands, one of which is coupled to strand 4 at one of the corner locations 6 at the front of shield 3 and the bands that form tensioning means 8 are then passed around the outside of the upper thigh of the wearer and are coupled with a strand 4 at the rear of shield 3 at the adjacent corner locations 6 on each side of shield 3. Flexible strand 4 may be permanently joined to shield 3 at positions intermediate the corner locations.

Figure 2:
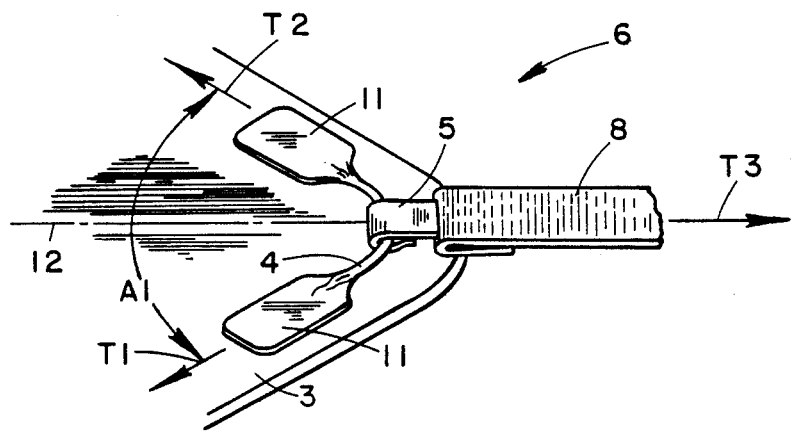
FIG. 2 is a fragmentary pictorial view of a preferred embodiment of a corner location of the suspension system of this invention.

FIG. 2 is a different embodiment which shows a view of a corner location 6 of a shield 3 wherein a flexible strand 4 is provided with securement surfaces 11 by means of which strand 4 may be joined to shield 3. Follower 5 is slideably engaged with strand 4. Follower 5 may then be caused to introduce tension in strand 4 by applying tension T3 in tensioning means 8. Tension T3 is converted to component vectors T1 and T2 which are directed towards the two adjacent corner locations 6 of shield 3 by virtue of the positioning of securement surfaces 11 on shield 3. Follower 5 is slideably engaged with strand 4 and therefore, disregarding frictional considerations, component vector T1 will equal component vector T2 so long as the line of force 12 of tension T3 lies in the angle A1 which is subtended by component vectors T1 and T2.

In a like manner, a similar tension T3 is applied to each of the corner locations 6 of shield 3, thereby creating a substantially balanced and equal tension around the perimeter of shield 3 while directing no tensioning forces towards the midspan of shield 3.

In FIG. 1, strand 4 is shown to be a continuous strand. In FIG. 2, strand 4 is shown to be an individual strand positioned at each corner location 6 and having its end segments secured to the shield and directed towards adjacent corners of shield 3. When the embodiment of FIG. 2 is employed, the perimeter of shield 3 serves to transmit the directed tensions around the perimeter between adjacent corner locations 6.

In counterdistinction to the directed tensions of the strand and sliding follower of this invention, the buttons and button holes, the sewn attachments, the tapes and other prior art corner attachments for perineal shields transmit the tensioning forces to the perineal shield along the line of force of the tensioning means. Prior art suspension systems for perineal shields tend, thereby, to pull the midspan of the shield against the body and to inhibit the blousing of the midspan.

Figure 3:
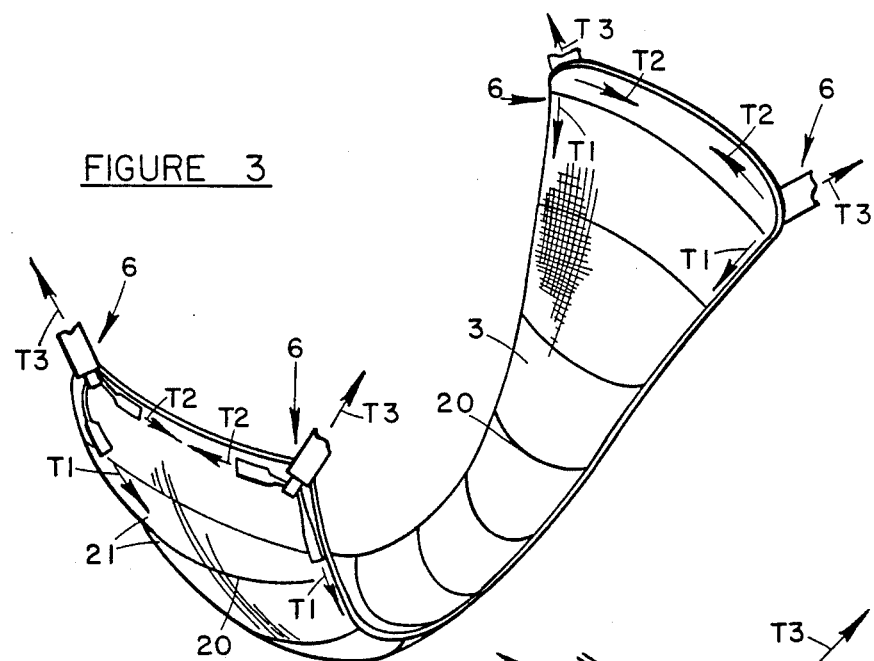
FIG. 3 is a partially schematic pictorial view of a shield employing the suspension system of this invention as the shield might appear in use.

Referring now to FIG. 3, substantially rectangular shield 3 is shown in the configuration that it tends to assume when positioned between the legs of a wearer. At each corner location 6, tension T3 is converted to component vectors T1 and T2 which direct the tensioning forces around the perimeter of shield 3. The perimeter of shield 3 is thereby maintained in uniform and comfortable intimate contact with a wearer's body around the perimeter of the shield. This continuous intimate contact tends to preclude the formation of gaps at the edges of the shield which commonly occur in prior art devices which rely upon folding or elastic gathers to attempt to conform to the wearer's anatomy.

In FIG. 3, lateral lines 20 have been drawn on substantially rectangular shield 3 to clearly illustrate the bloused configuration that shield 3 will take when in position between the legs of a wearer. This blousing of untensioned midspan 21 of shield 3 provides room for the genitalia in a manner that is comfortable and discreet. The blousing of midspan 21 along with the reliable maintenance of continuous and intimate contact between the perimeter of shield 3 and the body of the wearer provides a security against leakage that is not provided by the prior art. That is; when a sudden, moderate to severe discharge of urine or an explosive discharge of low viscosity stools occurs using one of the prior art devices, the discharges accumulate at a rate that is greater than can be absorbed or distributed reliably. Free liquid then accumulates between the body of the wearer and the shield. Because the free midspan 21 of shield 3 has capacity to contain the accumulating material and because the perimeter of shield 3 is maintained in continuous and intimate contact with the body of the wearer, the accumulating material will be contained until it can be distributed and absorbed or in other ways dealt with in a satisfactory fashion.

Numerous variations of the above described invention are possible and within the scope of this invention.

Figure 6:
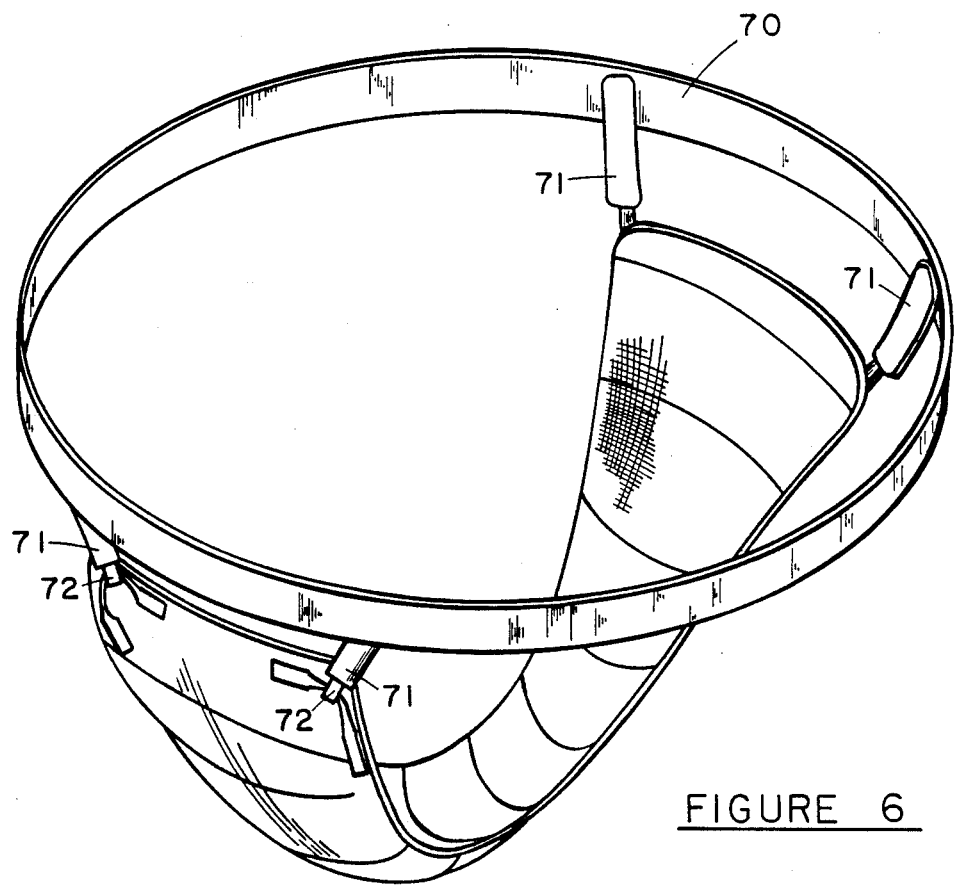
FIG. 6 is a pictorial view of a preferred embodiment of this invention having a waist encircling band.

For example, the tensioning means may be a pair of elastic bands which pass around the outside of the thighs of the wearer and join front corners of the shield with adjacent back corners of the shield. The tensioning means may also, as illustrated in FIG. 6, be a band 70 closely encircling the waist of a wearer and having depending therefrom elastic bands 71 having at their free end means for joining the the free ends with followers 72. These and other tension providing means are commonly used for providing tension to devices worn in the vicinity of the lower abdomen. These devices and modifications of these devices can serve as the tensioning means for the suspension system of this invention.

The physical configurations of the flexible strand, the follower which is slidably engaged with the strand, the means for joining the strand with the shield and the means for connecting the follower with the tensioning means may take many shapes, characteristics and combinations without departing from the scope of this invention.

Figure 4:
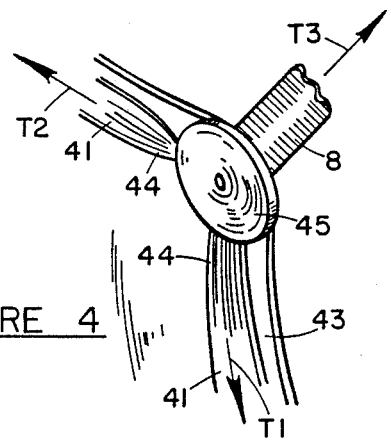
FIG. 4 is a fragmentary pictorial view of another preferred embodiment of a corner location showing elements functionally similar to those of FIG. 2.

For example, in FIG. 4, tensioning means 8 has a follower button 45 secured to its free end and shield 43 has flexible ribbon strand 44 adhered to shield 43 at securement surfaces 41. Follower button 45 is slidably engaged with flexible ribbon strand 44 so as to resolve tension T3 into directed tensions T1 and T2 in a manner similar to that described in relation to FIGS. 1 and 2.

Figure 5:
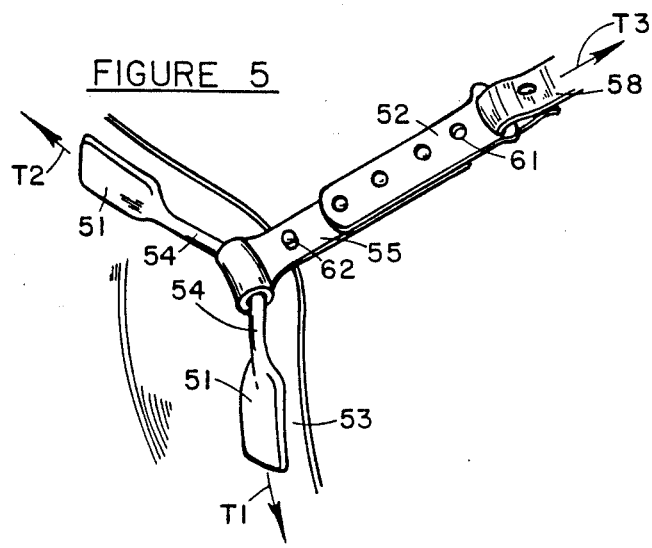
FIG. 5 is a fragmentary pictorial view of another preferred embodiment of a corner location showing elements functionally similar to those of FIG. 2.

In FIG. 5, tensioning means 58 has secured to its free end a coupling member 52 and shield 53 has flexible tubing strand 54 which is flattened at both ends to form securement surfaces 51 which are attached to the surface of shield 53. Coupling follower 55 is slidably engaged with strand 54 so as to resolve tension T3 into directed tensions T1 and T2 in a manner similar to that described in relation to FIGS. 1 and 2. Coupling member 52 is provided with a multiplicity of latching holes 61 and follower 55 is provided with latching projections 62 which are engageable with latching holes 61 of coupling member 52. Coupling member 52 may thereby be joined with follower member 55 at a number of locations and a means for adjusting the tension in tensioning means 58 is thereby provided.

Although it is not essential, it is preferred that the crotch shield be made of a moisture impervious material such as polyethylene fiilm. This would normally have a moisture absorbent pad positioned on the body facing side of the shield.

It can be seen that the elements that comprise the self adjusting suspension system of this invention may be present in many combinations. Therefore, it should be understood that the scope of this invention should not be limited to that of the above enabling disclosure and recitations of preferred embodiments. The scope of this invention should be limited only by the appended claims and all equivalents thereto that would become apparent to one skilled in the art.

I claim:

1. A self-adjusting perineal shield which comprises:
  a crotch shield means having four corner locations and a flexible midspan, each corner location having an individual flexible elastic strand associated therewith, said strand generally following the contour of the corner, each strand having end portions joined to the shield and an intermediate portion free for attachment to a coupling means;
  an elastic tensioning means to be worn in the waist area of a user; and
  coupling means to slidably connect the tensioning means to the elastic strand at each corner of the shield and transmit tensioning forces thereto, the coupling means dividing the strand into two segments at a given corner with with a first segment oriented toward and directing forces to a first adjacent corner and the second segment oriented toward and directing forces to a second adjacent corner, so that the tensioning forces transmitted from the tensioning means to the strand are directed along the perimeter of the shield without introducing substantial forces acting on the flexible midspan of the shield.

2. The perineal shield of claim 1 in which the tensioning means comprises two elastic strips, each strip having a coupling means at each end for attachment to the flexible strand at a corner location, so that when the perineal shield is in use each strip passes around the outside of a thigh of a wearer and joins a front corner of the shield to an adjacent back corner.

3. The perineal shield of claim 1 in which the tensioning means is a waistband having four spaced apart elastic strips depending therefrom, each strip having a free end with a coupling means for attachment to the elastic strand at a corner of the device.

4. The perineal shield of claim 1 in which the coupling means are hooks removably engagable with the flexible strand.

5. The perineal shield of claim 1 in which the crotch shield serves as an incontinence protection device.

6. The perineal shield of claim 1 in which the crotch shield is moisture impervious.

7. The perineal shield of claim 6 in which the crotch shield further includes a moisture absorbent body facing portion.

* * * * *